United States Patent
Lafond et al.

(10) Patent No.: US 6,206,872 B1
(45) Date of Patent: Mar. 27, 2001

(54) ENDOSCOPIC INSTRUMENT WHICH CAN BE BENT

(75) Inventors: Christophe Lafond, Vichy; Alain Tanguy, Clermont-Ferrand, both of (FR); Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 0 days.

(21) Appl. No.: 09/214,266

(22) PCT Filed: Jun. 24, 1997

(86) PCT No.: PCT/DE97/01309

§ 371 Date: May 3, 1999

§ 102(e) Date: May 3, 1999

(87) PCT Pub. No.: WO97/49342

PCT Pub. Date: Dec. 31, 1997

(30) Foreign Application Priority Data

Jun. 24, 1996 (DE) .............................. 196 25 241

(51) Int. Cl.⁷ .................................. A61B 17/00
(52) U.S. Cl. .............. 606/1; 606/170; 606/174; 606/205

(58) Field of Search ................... 600/146; 606/1, 606/170, 174, 205; 227/19; 81/177.6, 177.8

(56) References Cited

U.S. PATENT DOCUMENTS

| | | | |
|---|---|---|---|
| 5,374,277 | * 12/1994 | Hassler | 606/207 |
| 5,520,678 | * 5/1996 | Heckele et al. | 606/1 |
| 5,772,655 | * 6/1998 | Bauer et al. | 606/1 |
| 5,797,900 | * 8/1998 | Madhanni et al. | 606/1 |
| 5,810,865 | * 9/1998 | Koscher et al. | 606/174 |
| 5,931,832 | * 8/1999 | Jensen | 606/1 |

* cited by examiner

Primary Examiner—John P. Leubecker
(74) Attorney, Agent, or Firm—St. Onge Steward Johnston & Reens LLC

(57) ABSTRACT

An endoscopic instrument has an external tube and a hollow cylinder coaxially extending along a longitudinal axis and actuatable to move axially in opposite directions to rotate a distal end of the instrument provided with an engaging element between angular positions. The distal end actuated by the outer tube is rotatable about a pin having an axis of rotation which is spaced radially from the longitudinal axis as another pin formed on and extending radially from the cylinder is guided along an arcuate groove provided on the distal end of the instrument.

17 Claims, 2 Drawing Sheets

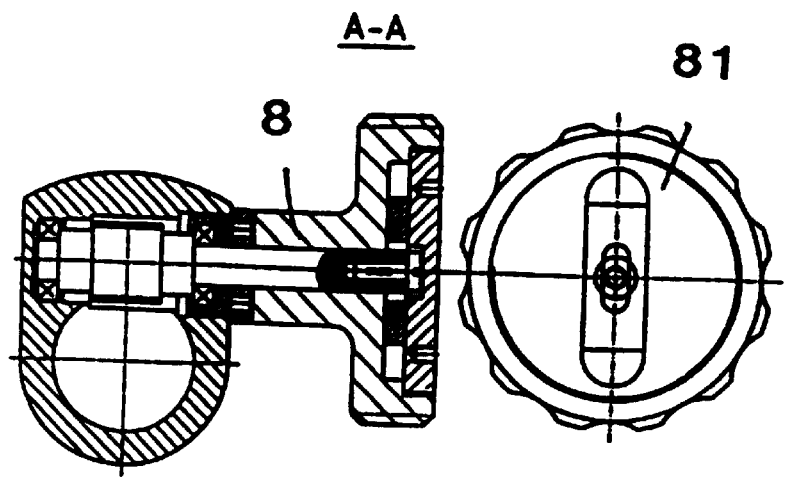
FIG. 2a  FIG. 2b
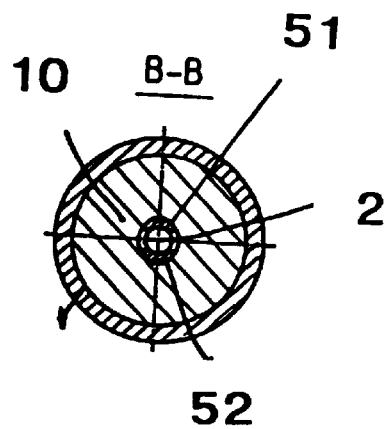
FIG. 3
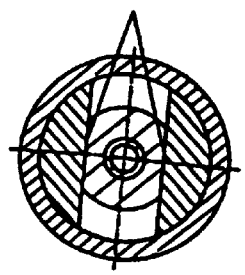
FIG. 4

ENDOSCOPIC INSTRUMENT WHICH CAN BE BENT

FIELD OF THE INVENTION

The present invention relates to a bendable endoscopic instrument having outer and inner coaxial tubes which are linearly displaceable in opposite directions along a common axis to provide effective pivotal displacement of the instrument's distal end having a pivot axis offset from the common axis.

PRIOR ART

Endoscopic instruments are known in which the distal end as a unit is bendable or pivotable relative to the longitudinal axis of the instrument. By way of example, reference is made to the following prior art documents which are explicitly referred to in all other respects for an explanation of all the details and applications which are not described here in depth: U.S. Pat. Nos. 5,318,528; 5,330,502; 5,354,311; German Patent DE 42 43 715 A1; German Patent DE 43 24 254 C1.

At the distal end a functional element of any kind may be mounted. This functional element is so connected via a rod to an actuating element disposed at the proximal end that the angular position of the functional element, such as the jaws of forceps or scissors, may be adjusted relative to the distal end which is suitable for bending or pivoting as a unit.

The instruments known from the aforementioned prior art documents present the disadvantage that either the distal end is not bendable over a wide field of traverse, or that the instruments require a comparatively substantial space because a single linearly displaceable actuator travels a substantial axial distance in order to pivotally displace the bendable end in a desirable position. As a result, these instruments are not suitable for application on the vertebrae of young people, for instance.

Moreover, the known instruments are not easy to sterilise.

BRIEF DESCRIPTION OF THE INVENTION

In accordance with the present invention it has now been detected that a particularly compact and at the same time stable endoscopic instrument is obtained when the axis of rotation of the distal end does not intersect with the longitudinal axis of the endoscope. With such an arrangement of the axis of rotation of the distal end, however, the problem arises that the position of the other element relative to the distal end pivotable as a unit varies as the angular position of the distal end relative to the longitudinal axis of the instrument varies. In accordance with the invention, therefore a compensating mechanism is provided which prevents a variation of the relative angular position of the other element, e.g. the jaws of forceps or scissors, when the distal end is bent or pivoted as a unit.

The inventive bendable instrument hence presents the advantage that the distal end may be pivoted over a wide field of movement—typically ±70 degrees and more—relative to the principal axis. And the instrument is yet so compact that it can be easily inserted into a standard-diameter trocar.

In another inventive embodiment which may or may not be combined with the the hollow cylinder which serves to transfer the pivoting movement of the distal end as a unit, is guided in a bayonet element on the distal side which is provided with a bayonet flange by which it may be inserted into a bayonet socket in an external tube.

This design ensures easy dismantling and excellent stability and safe guidance and, above all, a defined assembly of the instrument after cleaning or sterilisation in the disassembled state.

In accordance with still another improvement the rod has a flexible design in the bending region in a manner known per se. The rod may have a rectangular cross-sectional area in particular, with the narrow side of the rectangle being orthogonal on the pivoting axis.

In accordance with another aspect of the invention, the rod presents a cross-sectional area in the bending region which is smaller than that in the non-bent region, having a round cross-sectional area, particularly in the common manner.

Still another feature of this invention the rod closes the jaws of the forceps, scissors, etc. or varies the angular position of the other element from the home position in response to traction or pressure in a manner known per se. The configuration of the rod as tie rod presents the particular advantage that the rod may also consist of a cable (Claim 4) at least in the bending region.

The invention further discloses an actuator element is provided on the proximal side which when actuated causes the distal end to bend or pivot, respectively. This actuator element may be a set screw in particular which displaces, via a threaded engagement, a hollow cylinder arranged concentrically with the rod and which operates a pivoting element which varies the angular position of the distal end and is preferably fixedly connected to the distal end. The pivoting element and the hollow cylinder may be operatively connected to each other, particularly via a pin engaged in a groove.

A further improvement in accordance with the invention is that the set screw turns, via a threaded engagement, an intermediate element which displaces the hollow cylinder via different threads and the external tube in a suitable manner for compensation in terms of length. The thread for driving the hollow cylinder may be a left-hand thread and the length-compensating thread may be a right-hand thread. The set screw may be displaced in concentric relationship with the longitudinal axis or at an angle of 90° relative to the longitudinal axis.

In the preferred improvement the distal end or the distal head is provided for rotation about the longitudinal axis into several indexed positions or locking positions so that the surgeon is able to set certain important angular positions rapidly. It is moreover expedient to have a stop or the like on the handle which makes it possible to release the head for rotation or lock it in a certain position.

In another aspect of the invention the hollow cylinder presents two opposing elastic bulges in its proximal terminal zone, which are used for insertion into recesses of a complementary shape in a tube prevented from rotation. This protection of the hollow cylinder from rotation and hence an opening of the bayonet lock is achieved via the inserted rod which prevents the bulges of the hollow cylinder from resilient engagement and hence a rotation or disassembly of the instrument.

The inventive instrument may be used for the most different medical operations. Its application in surgical operations for coelioscopy or endoscopy, respectively on the vertebrae of young patients is particularly expedient, in which cases the introduction of the endoscopic instruments from the anterior side of the thorax is to be preferred because operations on the posterior section of the vertebrae, specifically in succession on several vertebrae, are then possible without the necessity to retract the instrument. The operations may be controlled from the region in the vicinity of the handle on account of the various rotational or pivoting movements.

BRIEF DESCRIPTION OF THE DRAWING

In the following, the invention will be described in more details by exemplary embodiments, without restriction of the general inventive idea, with reference to the drawing, which is explicitly referenced in all other respects as far as the disclosure of all inventive details is concerned which are not explained thoroughly in the text. In the drawing:

FIGS. 1b and 1c illustrate enlarged details of FIG. 1a,

FIGS. 2a, 3 and 4 are each a cross-sectional view taken through the element illustrated in FIG. 1a at the locations a—a, b—b and c—c, and FIG. 2b is a plan view on the sectional plane a—a.

DESCRIPTION OF AN EMBODIMENT

Figure 1A:
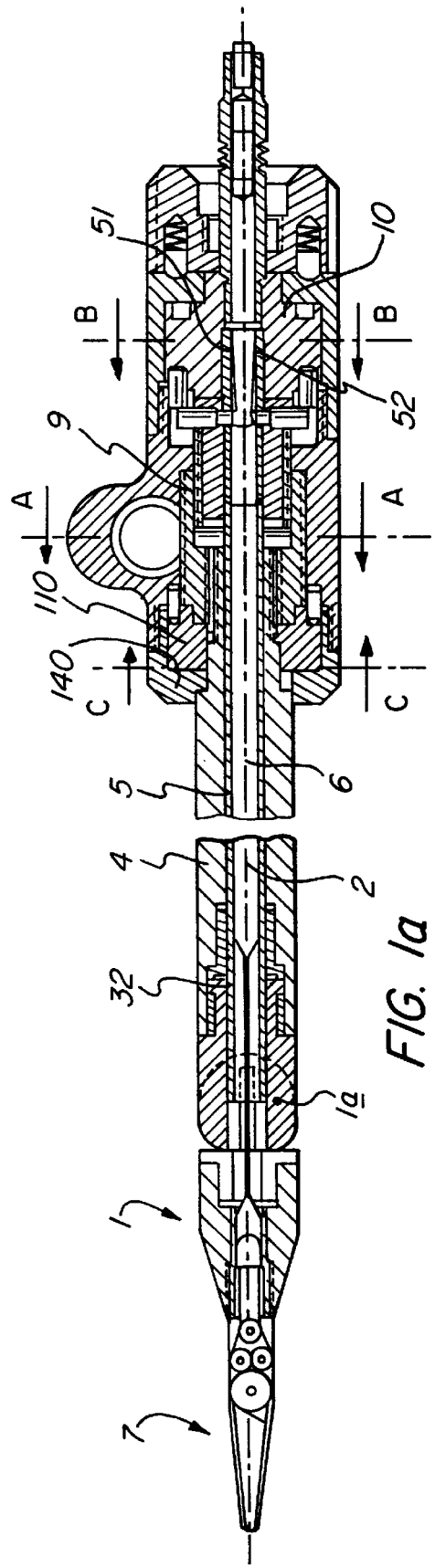
FIG. 1a is a longitudinal sectional view taken through an inventive instrument.
Figure 1C:
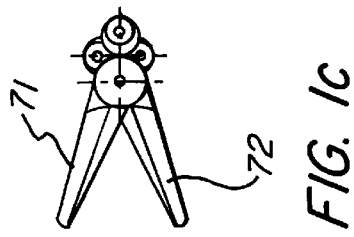
Figure 1B:
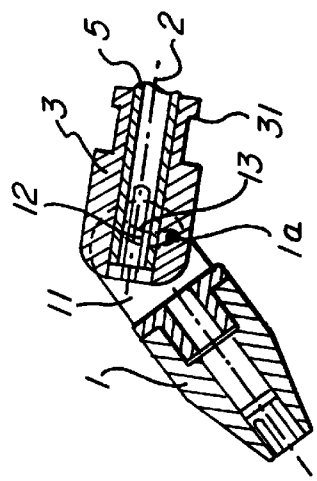

An endoscopic instrument illustrated in FIG. 1 includes coaxially positioned an external tube 4 and an internal hollow cylinder 5 which extend along a center axis 2. As will be explained in detail hereinbelow, opposite axial displacement of the tube and the cylinder causes the distal end 1 of the instrument to move axially and rotatably to bring an engaging element 7 in at least one angular position, as shown in FIG. 1b.

Particularly, the distal end 1 includes a pivoting element 11 formed with a curved groove 12 and a bayonet flange 31, which detachably engages a bayonet socket 32 of the external tube 4 for axial displacement therewith. Due to the bayonet connection, the bayonet flange 31 is axially aligned with the external tube and the cylinder 5 during their displacement.

In accordance with the invention, the bayonet flange 31 and the pivoting element 11 are rotatably interconnected by means of a pin 1a extending along a rotation axis which is spaced radially from the longitudinal axis 2. As a consequence, the pivoting element and the bayonet flange 31 angularly move relative each other about the pin 1a upon applying an external torque. This is accomplished by a cam mechanism including the above-mentioned groove 12 and a pin 13 extending radially outwardly from the cylinder 5 and slidably engaging the groove.

The structure, as described above, allows the pin 13 to follow a curved path of the groove's surface as the cylinder 5 moves toward the distal end while the external tube 4 and the distal end are displaced toward a proximal end of the endoscopic instrument. As a result, the pivoting element 11 rotates relative to the rest of the structure about the pin 1a in at least one angular position. Critical to the invention is the fact that an axial stroke, at which both the tube 4 and the cylinder 5 are displaced, is relatively short compared to an instrument in which such pivotal displacement is caused by a single axially displaceable actuator.

A rod 6 is guided in the hollow cylinder 5, which is connected to an actuator element, e.g. two hand-pieces or a thumb-operated lever, which is disposed on the proximal side and not illustrated here. The operation of the actuator elements on the proximal side causes a variation of the angular position of the engaging element disposed on the distal side relative to the element pivotable as a unit, which engaging element is provided in the form of scissors in the embodiment illustrated here, without a restriction of the general inventive idea.

FIG. 1c illustrates a possibility of operation of the scissors jaws 71 and 72.

With the axis of rotation 1a of the distal end 1, which can be rotated or bent as a unit, not intersecting the longitudinal axis 2 of the endoscopic instrument, a pivoting or rotating movement would cause a variation of the angular position of the engaging element 7 provided on the distal side relative to the distal end 1.

In accordance with the invention therefore a compensating mechanism allowing the external tube and the hollow cylinder to have short axial displacement is provided.

A setting element is provided for adjustment of the angular position of the distal end 1, which is configured as a set screw 8 (FIG. 2a). FIG. 2b is a plan view on the actuating button 81 of the set screw 8. The set screw is connected via a thread connector to an intermediate element 9. The intermediate element 9 rotatable about the axis 2 due to actuation of the set screw 8 to axially displace the hollow cylinder 5 via a left-hand thread and the external tube 4 via a right-hand thread. The thread pitches are so dimensioned that the tube 4 and the cylinder 5 travel a short distance and bring the distal end 1 in a desirable angular position upon a fewer turns of the set screw 8. Pins are provided for operation of the hollow cylinder or the external tube, respectively, which are supported on respective bearing faces.

At its proximal end the hollow cylinder 5 is provided with two opposite elastic bulges 51 and 52 for protection from rotation. The cylinder can be inserted via these bulges 51 and 52 into recesses of a tube 10 of complementary shape. Upon reaching a desirable angular position of the distal end 1, the rod 6 can be pushed toward the distal end through the cylinder 5. The rod is sized to have differently sized segments of its outer surface with a relatively large surface pressing against the bulges 51 and 52 in order to displace them radially outwardly, as shown in FIG. 4, thereby arresting further axial displacement of the cylinder 5 which, thus, locks the pivoting element 11 along with the engaging element in a desirable angular position.

As shown in FIG. 4, the instrument has an outer annular sleeve 140 receiving an annular element 110 which has flat axial inner surfaces formed complimentary to flat surfaces of the external tube 4. Thus, rotation of the set screw 8 can impart only axial linear displacement to the tube 4.

What is claimed is:

1. An endoscopic instrument extending along a longitudinal axis and having a proximal end, comprising:
    an inner hollow sleeve extending along the longitudinal axis;
    a rod traversing the inner sleeve and having an engaging element mounted on a distal end of the rod;
    an outer sleeve coaxial with and spaced radially outwardly from the inner sleeve;
    an actuator simultaneously displacing the outer and inner sleeves in opposite axial directions; and
    a pivot extending along the distal end of the rod and rotatable with the engaging element about a rotation axis extending perpendicular to the longitudinal axis and spaced radially therefrom between a first position, wherein the engaging element is aligned with the inner and outer sleeves, and at least one second position, wherein the engaging element is inclined with respect to the sleeves upon axial displacement of the of the outer and inner sleeves.

2. The instrument defined in claim 1 wherein the pivot includes a bayonet flange mounted pivotally thereon and engaging a bayonet socket of the outer sleeve to provide axial displacement of the pivoting element upon axial displacement of the external tube.

3. The instrument defined in claim 1 wherein the inner sleeve has a radially outwardly extending pin and the pivot has a curved groove engageable by the pin upon axial displacement of the sleeves and guiding the pin to have the pivot angularly displace between the first and one second positions.

4. The instrument defined in claim 1 wherein the inner sleeve has a curved groove and the pivot has an inwardly extending radial pin engaging the curved groove which provides a cam surface allowing the pivot to rotate between the first and one second positions.

5. The instrument defined in claim 1 wherein the outer sleeve has a rod extending along the axis of rotation and rotatably attached to the pivot to rotate about the axis of rotation upon displacement of the inner and outer sleeves.

6. The instrument defined in claim 1 wherein the actuator includes a set screw and an intermediate shaft provided with two segments which have a left-hand thread and a right-hand thread, respectively, each of the left- and right-hand threads engaging a respective thread of the outer and inner sleeves to simultaneously displace them in opposite directions.

7. The instrument defined in claim 6 wherein the right- and left-hand threads have thread pitches sized to provide a uniform axial stroke for the inner and outer sleeves.

8. The instrument defined in claim 6 wherein the set screw has a thread connector threadedly engageable with the intermediate shaft.

9. The instrument defined in claim 8 wherein the thread connector is concentric with the inner and outer sleeves.

10. The instrument defined in claim 8 wherein the thread connector extends perpendicular to the longitudinal axis of the instrument.

11. The instrument defined in claim 6 wherein the set screw is rotatable between predetermined angular positions corresponding to the one and ant at least one another angular positions of the pivot.

12. The instrument defined in claim 1 further comprising a tube spaced receiving a proximal end of the inner cylinder which has a plurality of radially extending resilient bulges.

13. The instrument defined in claim 12 wherein the rod a proximal end sized to press the bulges against an inner surface of the tube to lock the axial displacement of the inner sleeve and being larger than a distal end of the rod.

14. The instrument defied in claim 1 wherein the rod is a flexible cord actuating the engaging element selected from the group consisting of forceps, scissors and the like.

15. A surgical instrument comprising:

an inner sleeve extending along a longitudinal axis and having a radially extending pin;

an outer sleeve coaxial with and spaced radially apart from the inner sleeve, the inner and outer sleeves being displaceable in opposite axial directions upon applying an external force;

a pivot having a tool holder, the pivot being axially displaceable with the outer sleeve and rotatable thereon to pivot about a pivot axis extending perpendicular to and radially offset from the longitudinal axis between a first position, wherein the pivot and the sleeves are axially aligned, and at least one second position, wherein the pivot is inclined relative to the sleeves; and a cam between the tool holder and the inner sleeve to provide the angular displacement of the pivot as the sleeves move in opposite axial directions.

16. The surgical instrument defied in claim 15 wherein the pivot further includes a bayonet flange pivotal relative one another about the pivot axis, the bayonet flange being axially connected to the outer sleeve for simultaneous axial displacement therewith.

17. The surgical instrument defined in claim 15 further comprising an actuator having a threaded shaft which is provided with left- and right hand threads engaging threads of the inner and outer sleeves, respectively, for simultaneous displacement thereof in opposite axial directions.

* * * * *